United States Patent [19]

Hasegawa

[11] Patent Number: 4,881,810

[45] Date of Patent: Nov. 21, 1989

[54] ENDOSCOPE WITH A REMOVABLE COVER MEMBER

[75] Inventor: Hiroshi Hasegawa, Hachioji, Japan

[73] Assignee: Olympus Optical Co., Ltd., Tokyo, Japan

[21] Appl. No.: 118,068

[22] Filed: Nov. 9, 1987

[30] Foreign Application Priority Data

Nov. 10, 1986 [JP] Japan .................................. 61-267258

[51] Int. Cl.⁴ ............................................ G02B 23/26
[52] U.S. Cl. .................. 356/241; 350/96.26;
128/4; 128/6
[58] Field of Search ....................... 356/241; 128/4, 6;
350/96.26

[56] References Cited

U.S. PATENT DOCUMENTS 4,676,230 6/1987 Miyazaki ................................. 128/4

Primary Examiner—Vincent P. McGraw
Assistant Examiner—S. A. Turner
Attorney, Agent, or Firm—Armstrong, Nikaido Marmelstein, Kubovcik & Murray

[57] ABSTRACT

An endoscope comprising an elongated insertable part, a rigid tip body provided in the tip part of the insertable part and having an observing window and illuminating window, an observing means for observing an object to be imaged by receiving a light from the object incident from the observing window and an illuminating means emitting an illuminating light from the illuminating window, wherein the insertable part has a removably fitted tubular outer cover covering the outer periphery of this insertable part, an annular fixing member fixing the outer cover in the tip part to the tip body is secured to the outer periphery of the tip body and has a slit provided in the axial direction and further a cuttable connecting part connecting the slit in the direction intersecting the axial direction is provided.

14 Claims, 6 Drawing Sheets

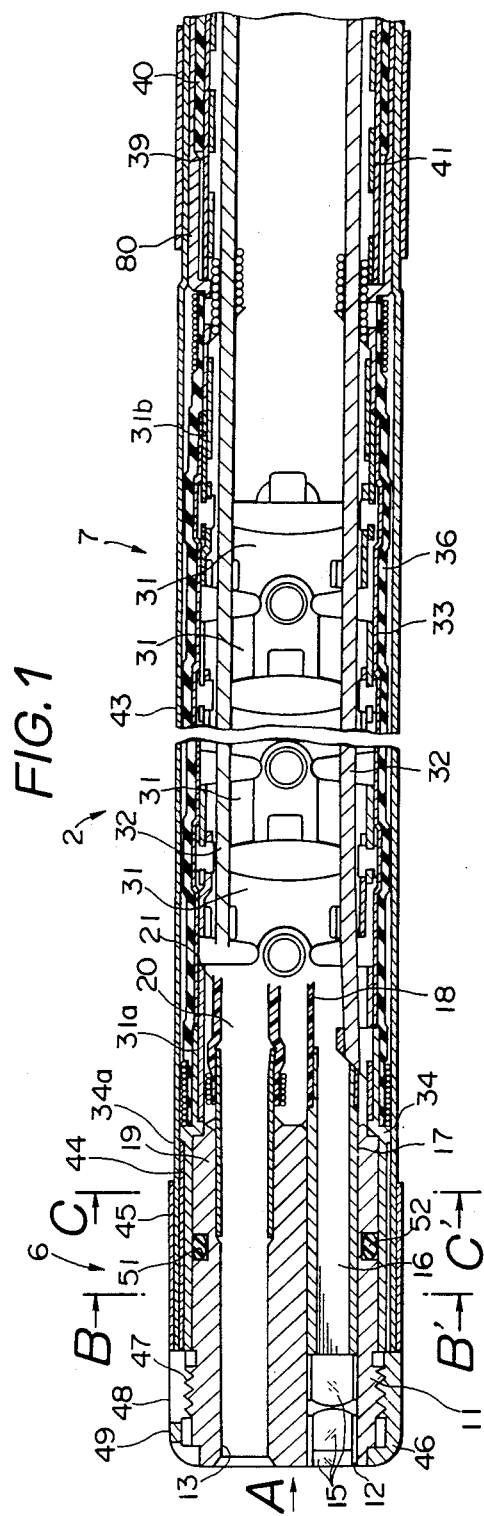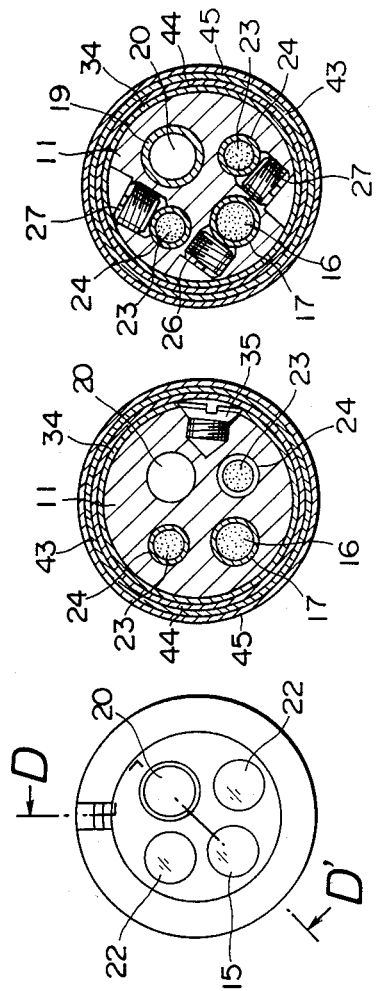

FIG.7(A)
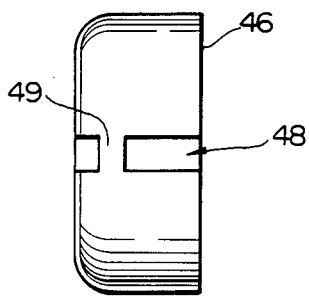
FIG.7(B)  FIG.7(C)  FIG.7(D)
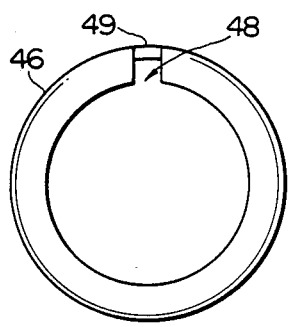 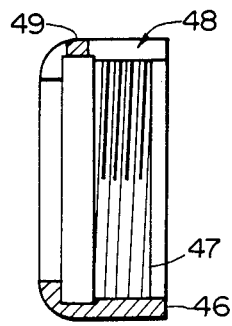 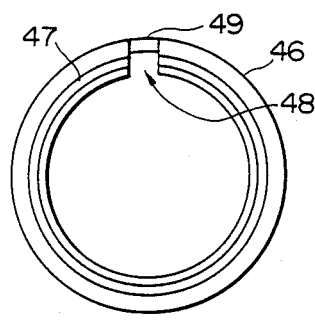
FIG.8  FIG.9
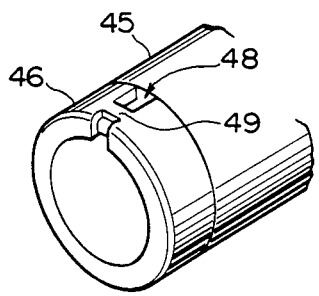 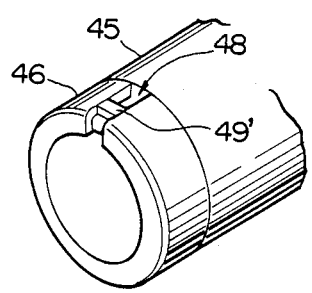

ENDOSCOPE WITH A REMOVABLE COVER MEMBER

BACKGROUND OF THE INVENTION:

1. Field of the Invention:

This invention relates to an endoscope wherein an outer cover covering an insertable part is removably fitted.

2. Related Art Statement:

Recently there is extensively used a medical endoscope to observe organs within a body cavity by inserting an elongated insertable part into the body cavity or to make various curing treatments by using forceps inserted through a forceps channel as required. In the industrial field, there is also extensively utilized an industrial endoscope to observe or inspect the interior of a boiler, turbine, engine, chemical plant or the like.

In the above mentioned industrial endoscope, the insertable part is protected with a protective outer fitted sheath made of a net tube (blades) or the like made by knitting such fine wires as of a metal to be like a net. This protective outer fitted sheath is removably fitted because, while it is repeatedly used, it will be worn and broken by friction or the like and, when a light guide or image guide is broken, it will have to be repaired.

In order to removably fix the above mentioned protective outside fitted sheath, conventionally it has been fixed on the tip side to the tip of an endoscope with screws or the like.

However, in case the above mentioned protective outer fitted sheath is fixed with screws, the screws or the like will be likely to accidentally drop into an object being inspected with an endoscope. If the protective outer fitted sheath is fixed with a bonding agent so that no screw may drop, it will be difficult to remove the sheath.

OBJECT AND SUMMARY OF THE INVENTION:

An object of the present invention is to provide an endoscope wherein screws or the like for fixing an outer cover will not drop and it is easy to fit and remove the outer cover.

The endoscope according to the present invention comprises an elongated insertable part, a rigid tip body provided in the tip part of this insertable part and having an observing window and illuminating window, an observing means for observing an object to be imaged by receiving a light from the object incident from the observing window and an illuminating means emitting an illuminating light from the illuminating window. The above mentioned insertable part has a removably fitted tubular outer cover covering the outer periphery of this insertable part. An annular fixing member fixing the above mentioned outer cover in the tip part to the above mentioned tip body is secured to the outer periphery of the above mentioned tip body and has a slit provided in the axial direction. A cuttable connecting part connecting the above mentioned slit in the direction intersecting the axial direction is further provided. Therefore, the outer cover can be fixed by the annular fixing member and can be removed by using the above mentioned slit to remove the outer cover.

Other features and advantages of the present invention will become apparent enough with the following explanation.

BRIEF DESCRIPTION OF THE DRAWINGS:

FIGS. 1 to 9 relate to the first embodiment of the present invention.

FIG. 1 is a vertically sectioned view showing an insertable part of an endoscope.

FIG. 2 is a view as seen in the direction indicated by the arrow A in FIG. 1.

FIG. 3 is a sectioned view on line B—B' in FIG. 1.

FIG. 4 is a sectioned view on line C—C' in FIG. 1.

FIG. 5 is a sectioned view showing the vicinity of a light guide in the tip part.

FIG. 6 is an explanatory view showing the entire endoscope.

FIG. 7(A) is a plan view of a cover member.

FIG. 7(B) is an elevation of the cover member.

FIG. 7(C) is a vertically sectioned view of the cover member.

FIG. 7(D) is a back view of the cover member.

FIG. 8 is a perspective view showing the cover member.

FIG. 9 is a perspective view of the cover member showing a modification of a connecting part.

FIG. 10 is a vertically sectioned view of a tip part.

FIG. 11 is a perspective view showing a cover member.

FIG. 12 is a vertically sectioned view of a tip part.

FIG. 13 is a perspective view showing a cover member.

FIG. 14 is a vertically sectioned view of a tip part.

FIG. 15 is a perspective view showing a cover member.

Figure 6:
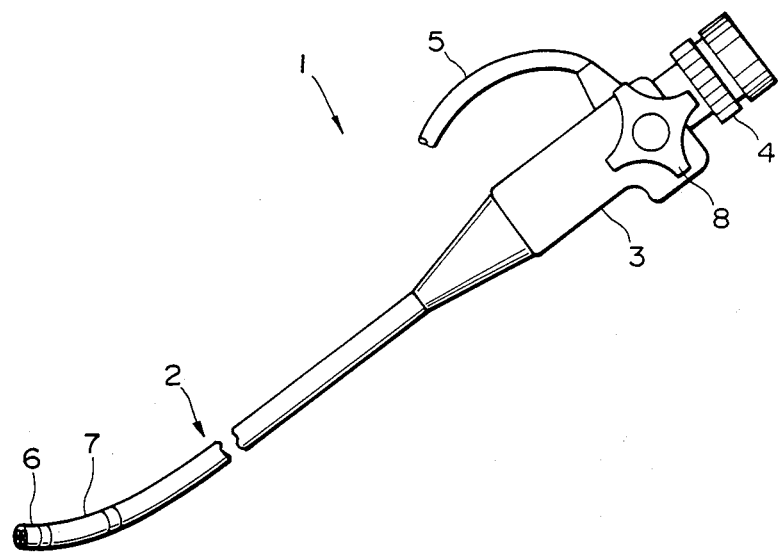

DETAILED DESCRIPTION OF THE PREFERRED EMBODIMENTS:

As shown in FIG. 6, an (industrial) endoscope 1 comprises an elongated insertable part 2, a large diameter operating part 3 connected to the rear end side of this insertable part 2, an eyepiece part 4 provided at the rear end of this operating part 3 and a light guide cable 5 extended out of the side of the above mentioned operating part 3.

A rigid tip part 6 is provided on the tip side of the above mentioned insertable part 2 and a curvable part 7 is provided on the rear side adjacent to this tip part 6. The above mentioned curvable part 7 can be curved vertically and horizontally by rotating a curving operation knob 8 provided on the above mentioned operating part 3. The above mentioned operating part 3 is provided with an inserting port not illustrated communicating with a treating tool channel provided within the above mentioned insertable part 2.

The above mentioned insertable part 2 is formed as shown in FIGS. 1 to 5.

The above mentioned tip part 6 is provided with a substantially columnar tip body 11 made of such rigid material as a metal. In this tip body 11, there are formed an observing through hole 12, treating tool channel through hole 13 and two illuminating through holes 14 all passing in parallel with the lengthwise direction of the above mentioned insertable part 2.

An objective lens system 15 is fitted in the above mentioned observing through hole 12. An image guide 16 of fibers high in the flexibility is arranged as an image transmitting means so as to have its tip surface positioned in a position in which an optical image of an object to be imaged is formed by this objective lens system 15. This image guide 16 of fibers is bundled on the tip side by a mouthpiece 17, is fitted to the above mentioned observing through hole 12, is covered with a flexible tube 18 and is inserted through the above mentioned insertable part 2 to transmit an optical image to the above mentioned eyepiece part 4.

On the other hand, a treating tool channel mouthpiece 19 is fitted on the rear end side of the above mentioned treating tool channel through hole 13 and a treating tool channel tube 21 forming the treating tool channel 20 is connected to the rear end of this treating tool channel mouthpiece 19.

Such triple layer tube as, for example, a Multi-Goatube (trade name of a product of Japan Goatex Company) has been so far used for this treating tool channel tube 21 in order to be water-tight but, in this embodiment, such single-layer tube as, for example, a Single-Goatube (trade name of a product of Japan Goatex Company) is used for this treating tool channel tube 21. The above mentioned Multi-Goatube is made by coating the outer periphery of a Single-Goatube with fluorine rubber and further coating the outer periphery of the coating with a Single-Goatube and is water-tight but has a defect that the diameter is large. The treating tool channel tube 21 of the industrial endoscope to be used within an engine or the like need not particularuly be water-tight, can be made thin by using a Single-Goatube, can have the other space than of the treating tool channel tube 21 within the insertable part 2 made wider and can have the above mentioned insertable part 2 made thinner.

This treating tool channel tube 21 is inserted through the above mentioned insertable part 2 and is connected to an inserting port not illustrated of the above mentioned operating part 3.

Figure 5:
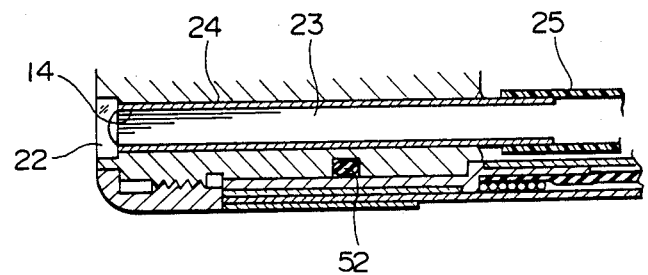

As shown in FIG. 5, a light distributing lens 22 is fitted to the tip part of the above mentioned illuminating through hole 1 and has a light guide 23 of fibers connected to the rear end. This light guide 23 of fibers is bundled on the tip side by a mouthpiece 24, is fitted to the above mentioned illuminating through hole 14, is covered with a flexible tube 25, is inserted through the above mentioned insertable part 2 and is connected to the above mentioned light guide cable 5.

As shown in FIG. 4, the above mentioned image guide 16 of fibers and light guide 23 of fibers are fixed to the above mentioned tip body 11 respectively with screws 26 and 27 screwed in from the outer peripheral side of the tip body 11.

Many substantially annular articulating frames 31 are rotatably connected in the lengthwise direction of the insertable part 2 within the curvable part 7 adjacent to the above mentioned tip part 6. For example, four operating wires 32 inserted through the above mentioned insertable part 2 and connected each at one end to the above mentioned curving operation knob 8 are connected each at the other end to the articulating frame 31a at the foremost end. By pulling and relaxing the above mentioned operating wires 32 by operating the above mentioned curving operation knob 8, the above mentioned curvable part 7 can be curved vertically and horizontally.

The above mentioned articulating frames 31 are housed within an inside net tube (blades) 33 made by knitting such fine wires as of a metal to be in the form of a net. The articulating frame 31a at the foremost end is internally fitted and fixed to the rear end of a cylinder 34. As shown in FIG. 3, this cylinder 34 is externally fitted to the above mentioned tip body 11 and is fixed to the above mentioned tip body 11 with a screw 35 on the tip side more than the position of fixing the above mentioned image guide 16 and light guide 23 to the above mentioned tip body 11 respectively with the screws 26 and 27.

In this embodiment, a groove 51 is formed peripherally on the outer periphery of the above mentioned tip body 11 between the screw fixing position of the above mentioned cylinder 34 and the screw fixing position of the above mentioned image guide 16 and light guide 23 and is fitted with an O-ring 52. The above mentioned cylinder 34 and tip body 11, that is, the tip part 6 and curvable part 7 can be kept liquid-tight between them by this O-ring 52. The tip part 6 and curvable part 7 have been so far kept liquid-tight between them. The screws 26 and 27 respectively for fixing the image guide 16 and light guide 23 to the tip body 11 have been set with a bonding agent around them so as to be water-tight in screw fixing and to be water-proof. Therefore, there has been a problem that it is difficult to remove the above mentioned screws 26 and 27 to make a repair. According to this embodiment, the tip part 6 and curvable part 7 can be kept liquid-tight between them, the above mentioned screws 26 and 27 are not water-tightly fixed and therefore the repair is easy.

The above mentioned inside net tube 33 is covered on the outer periphery with such tube 36 high in the flexibility as of rubber so as to be easy to curve. This tube 36 is bonded at both ends with a bonding agent, for example, after being wound with a thread so as to be fixed liquid-tightly.

A mouthpiece 80 is connected to the rear end of the articulating frame 31b at the last end. The net tube 39 and a flexible tube 40 made of a resin or the like and covering this net tube 39 are internally fitted and fixed at the front ends to this mouthpiece 80. A flexible spiral tube 41 formed by spirally winding a long shet-like member is housed on the inner periphery of the above mentioned net tube 39. The above mentioned image guide 16, light guide 24 and treating tool channel tube 19 are inserted through this inside.

The tube 36 of the above mentioned curvable part 7 and the above mentioned flexible tube 40 forming the insertable part 2 are covered on the outer peripheries with a protective outer fitted sheath 43. This protective outer fitted sheath 43 is held at the front end by an inner tube 44 and outer tube 45.

In this embodiment, a step 34a is peripherally formed on the outer periphery of the above mentioned tube 34 externally fitted to the above mentioned tip body 11. The above mentioned inner tube 44 is engaged with this step 34a.

A substantially cylindrical cover member 46 is externally fitted and fixed on the tip side of the above mentioned tip body 11. The above mentioned inner tube 44, outer tube 45 and protective outer fitted sheath 43 held by them are pressed in the tip parts and the above mentioned inner tube 44 is held by the above mentioned cover member 46 and the step 34a of the above mentioned tube 34 to fix the above mentioned protective outer fitted sheath 43.

The above mentioned cover member 46 is made as shown in FIGS. 7(A), (B), (C) and 8.

As shown in these drawings, the above mentioned cover member 46 is provided on the inner periphery with a female screw 47 to be screwed with a male screw provided on the outer periphery of the above mentioned tip body 11 and is bonded with a bonding agent to be fixed to the above mentioned tip body 11.

Also, in this embodiment, the above mentioned cover member 46 is provided with a slit 48 in the axial direction and further with a connecting part 49 connecting the above mentioned slit 48 in the direction intersecting the axial direction. This connecting part 49 is formed to be thin so as to be able to be cut with a file or the like. By the way, in the example shown in FIGS. 7 and 8, the above mentioned connecting part 49 is formed integrally with the cover member 46 and the above mentioned slit 48 is so formed as to divide the above mentioned cover member 46 in the direction intersecting at right angles with the axial direction by leaving this connecting part 49 but, as shown in FIG. 9, the slit 48 is provided so as to divide the above mentioned cover member 46 in the direction intersecting the axial direction and another member than the above mentioned cover member 46 may be bonded to the above mentioned cover member 46 so as to connect the above mentioned slit 48 to form a connecting part 49'.

In this embodiment formed as in the above, the inner tube 44, outer tube 45 and protective outer fitted sheath 43 held by them are pressed at the tips by the rear end of the cover member 46 and the above mentioned inner tube 44 is held by the rear end of the above mentioned cover member 46 and the step 34a of the above mentioned cylinder 34 to fix the above mentioned protective outer fitted sheath 43.

As the cover member 46 is fixed to the above mentioned tip body 11 by screwing and bonding, even if a force is applied in the direction of pulling the cover member 46 off the tip member 11 or a torque is applied in the direction of unscrewing the cover member 46, the cover member 46 will not easily drop off the tip body 11. As there is the above mentioned connecting part 49, even if a force is applied to expand the above mentioned slit 48, the slit 48 will not expand and the cover member 46 will not drop off.

In the case of removing the above mentioned protective outer fitted sheath 43 for a repair or the like, the connecting part 49 connecting the slit 48 of the above mentioned cover member 46 is cut by using a file or the like. Then, a screw driver or the like is inserted into the above mentioned slit 48, the slit 48 is opened and the cover member 46 is removed. By disengaging the cylinder 34 of the tip part of the protective outer fitted sheath 43 held by the inner tube 44 and outer tube 45 with the step 34a, the protective outer fitted sheath 43 can be removed.

Thus, according to this embodiment, as a screw or the like is not used to fix the above mentioned protective outer fitted sheath 43, no screw will drop during the inspection and it will be easy to remove the protective outer fitted sheath 43.

Figure 10:
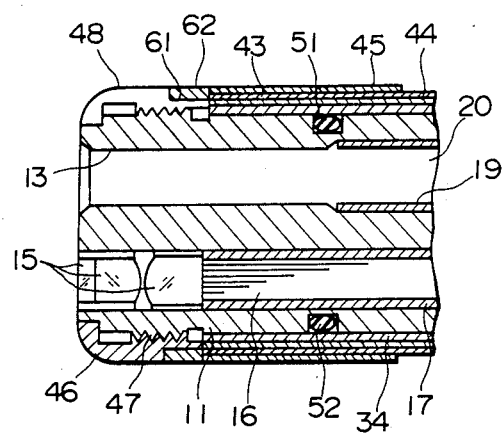
FIGS. 10 and 11 relate to the second embodiment of the present invention.
Figure 11:
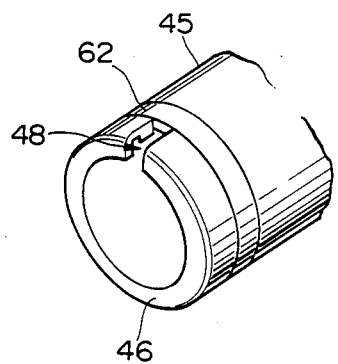

The second embodiment of the present invention is shown in FIGS. 10 and 11.

In this embodiment, the cover member 46 is provided with a slit 48 in the axial direction and with a wide groove 61 peripherally in the outer peripheral part, for example, on the rear end sude. By externally fitting a wide ring-like member 62 in this groove 61, the above mentioned slit 48 is connected in the direction intersecting the axial direction.

In this embodiment, in the case of taking out the protective outer fitted sheath 43, the ring-like member 62 connecting the slit 48 of the above mentioned cover member 46 is cut off by using a file or the like. The same as in the first embodiment, a screw driver or the like is inserted into the above mentioned slit 48, the slit 48 is opened and the cover member 46 is taken out. By disengaging the cylinder 34 of the tip part of the protective outer fitted sheath 43 held by the inner tube 44 and outer tube 45 with the step 34a, the protective outer fitted sheath 43 is removed.

The other formation, operation and effect are the same as in the first embodiment.

Figure 12:
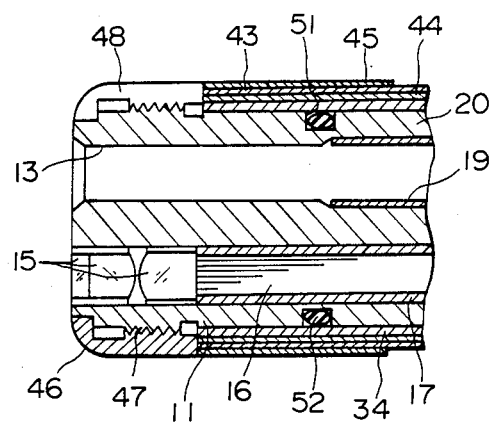
FIGS. 12 and 13 relate to the third embodiment of the present invention.
Figure 13:
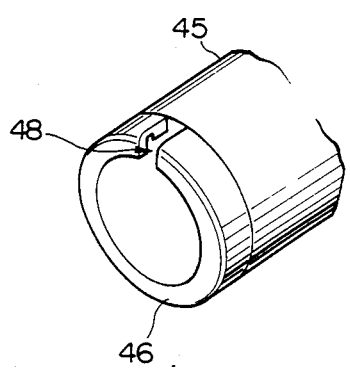

The third embodiment of the present invention is shown in FIGS. 12 and 13.

In this embodiment, the cover member 46 is provided with only the slit 48 in the axial direction but with no such connecting part connecting the slit 48 as is shown in the first and second embodiments. Therefore, in this embodiment, in the case of removing the cover member 46, a screw driver or the like is inserted into the above mentioned slit 48 and this slit 48 may be opened.

By the way, in this embodiment, as no connecting part is provided but the cover member 46 is fixed to the tip part 11 by screwing and bonding, the cover member 46 will not easily drop off the tip body 11.

The other formation, operation and effect are the same as in the first embodiment.

Figure 14:
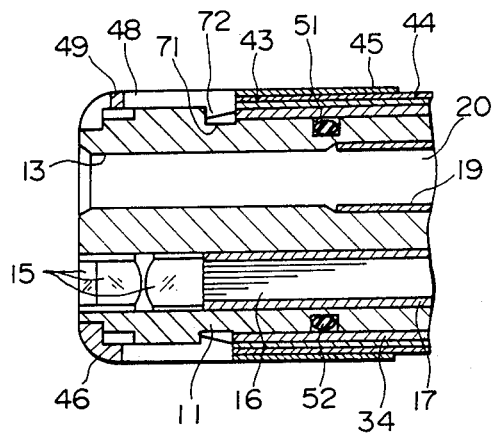
FIGS. 14 and 15 relate to the fourth embodiment of the present invention.
Figure 15:
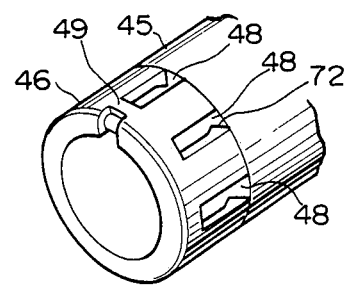

The fourth embodiment of the present invention is shown in FIGS. 14 and 15.

In this embodiment, the cover member 46 is externally fitted to the tip body 11 and is fixed to the tip body 11 by bonding with a bonding agent.

A peripheral groove 71 is formed on the outer periphery of the above mentioned tip body 11 corresponding to the rear end position of the above mentioned cover member 46.

On the other hand, in the position corresponding to the above mentioned groove 71 of the rear end of the above mentioned cover member 46, an engaging projection 72 expanded out in the inside diameter direction so as to be engaged with the above mentioned groove 71 when externally fitted to the above mentioned tip body 11 is peripherally formed. The above mentioned cover member 46 is provided with a plurality of slits 48 in the axial direction so as to be elastically deformable on the rear end side. By the way, the above mentioned engaging projection 72 is formed on the inner peripheral surface to be of a tapered surface larger in the diameter on the rear end side so as to be pressed on the outer periphery of the tip body 11 to be easily expanded outside in case the cover member 46 is to be externally fitted to the tip body 11 and not to be easily disengaged after it is engaged with the above mentioned groove 71. At least one of the slits 48 is provided in the direction intersecting the axial direction with the connecting part 49 connecting the slit 48 the same as in the first embodiment. The slit 48 provided with this connecting part 49 is formed to divide the above mentioned cover member 46 in the direction intersecting at right angles with the axial direction by leaving the above mentioned connecting part 49. The other slits 48 are formed to be of a predetermined length toward the tip side from the rear end of this cover member 46 without dividing the cover member 46.

In this embodiment of such formation, in assembling it, the cover member 46 is externally fitted and bonded to the tip body 11. When the above mentioned cover member 46 is to be externally fitted to the tip body 11, when the engaging projection 72 of the cover member 46 passes on the tip side in front of the groove 71 of the tip body 11, the cover member 46 will be elastically deformed in the expanded diameter direction on the rear end side but, on the other hand, when the above mentioned engaging projection 72 comes to the above mentioned groove 71, this engaging projection 72 will engage with the groove 71 and the cover member 46 will return to be of the original diameter on the rear end side. Thus, the above mentioned cover member 46 will be positively fixed to the tip body by the engagement of the above mentioned engaging projection 72 with the groove 71 and the bonding effect.

As the cover member 46 is bonded to the tip body 11, even if a force is applied to expand the cover member 46 on the rear end side having the engaging projection 72, the cover member 46 will not expand on the rear end side and, even if it is expanded on one of the rear end sides divided by the slits 48, unless it is simultaneously expanded on the remaining rear end sides, the engaging projection 72 will not be disengaged with the groove 71.

In this embodiment, in the case of removing the cover member 46, the same as in the first embodiment, the connecting part 49 connecting the slit 48 formed to divide the above mentioned cover member 46 is cut by using a file or the like. A screw driver or the like is inserted into the above mentioned slit 48 to open this slit 48 and the cover member 46 is removed.

The other formation, operation and effect are the same as in the first embodiment.

By the way, the present invention is not limited to the above mentioned embodiments. For example, the number of the slits 48 provided in the cover member 46 in each of the first and second embodiments may be plural.

The present invention can be applied not only to the industrial endoscope but also to the medical endoscope.

As explained above, according to the present invention, an annular fixing member fixing an outer cover is secured to a tip part of an insertable part and is provided with a slit in the axial direction and further with a cuttable connecting part connecting the above mentioned slit in the direction intersecting the axial direction and therefore there are effects that screws or the like for fixing the outer cover will not drop off and that the outer cover can be easily removed.

In this invention, it is apparent that working modes different in a wide range can be formed on the basis of this invention without deviating from the spirit and scope of the invention. This invention is not restricted by its specific working mode except being limited by the appended claims.

What is claimed is:

1. An endoscope comprising:
   an elongated tubular part for observing an object, said elongated tubular part having a rigid tip body at a tip part thereof;
   at least one tubular outer cover slidably positioned around the outer periphery of said elongated tubular part; and
   a removable cylindrical cover member firmly self-secured around said rigid tip body for retaining said at least one tubular outer cover, said cover member being provided with at least one substantially through slit along the longitudinal axis thereof, wherein said cover member is removed from said rigid tip body by forcibly expanding said slit in order to further remove said at least one tubular cover from said elongated tubular part.

2. The endoscope according to claim 1, wherein said removable cover member further has a cuttable connecting part at least across said slit, and said connecting part can be disconnected when said slit is forcibly expanded.

3. The endoscope according to claim 2, wherein said removable cover member and said cuttable connecting part form an integral single part.

4. The endoscope according to claim 2, wherein said cuttable connecting part is a part independent from said removable cover member.

5. The endoscope according to claim 4, wherein said cuttable connecting part is a ring-like member covering the outer periphery of said removable cover member.

6. The endoscope according to claim 1, wherein said rigid tip has an observing window and an illuminating window, and said elongated tubular part has an observing means for observing an object by receiving light from said object through said observing window and further has an illuminating means for illuminating light from said illuminating window.

7. The endoscope according to claim 6, wherein said observing means has an objective lens system receiving light reflected from said object, an eyepiece part connected to said elongated tubular part at the end opposite to said tip part and an image guide fibers placed within said elongated tubular part for transmitting light from said objective lens system to said eyepiece.

8. The endoscope according to claim 6, wherein said illuminating means has light guide fibers placed within said elongated tubular part for transmitting illuminating light from a light source to said illuminating window.

9. The endoscope according to claim 1 or 6, further comprising a treating tool channel of a single-layer tube.

10. The endoscope according to claim 6, wherein said tip body is provided with a plurality of independent holes through which said observing means and said illuminating means are inserted.

11. The endoscope according to claim 1, wherein there are a plurality of slits.

12. The endoscope according to claim 1, wherein said elongated tubular part is provided with a curvable part adjacent to said tip part thereof.

13. The endoscope according to claim 1, wherein said elongated tubular part includes an image guide fibers and light guide fibers.

14. The endoscope according to claim 1, wherein said tip body has a peripheral groove around the outer periphery thereof and a O-ring is fitted therein.

* * * * *

UNITED STATES PATENT AND TRADEMARK OFFICE
CERTIFICATE OF CORRECTION

PATENT NO. : 4,881,810

DATED : November 21, 1989

INVENTOR(S) : Hiroshi HASEGAWA

It is certified that error appears in the above-identified patent and that said Letters Patent is hereby corrected as shown below:

On the cover page, Item [30] after "61-267258" add:

--Oct. 19, 1987 [JP] Japan.....................62-265124--.

Signed and Sealed this

Eighteenth Day of December, 1990

Attest:

HARRY F. MANBECK, JR.

*Attesting Officer*  *Commissioner of Patents and Trademarks*